United States Patent [19]

Gügel et al.

[11] Patent Number: 5,763,719
[45] Date of Patent: Jun. 9, 1998

[54] THERMALLY STABLE FULLERENE DERIVATIVES AND PROCESS FOR PRODUCING THE SAME

[75] Inventors: Andreas Gügel, Mainz; Pavel Belik, Rodenbach; Klaus Müllen, Mainz, all of Germany

[73] Assignee: Hoechst AG, Frankfurt, Germany

[21] Appl. No.: 492,021

[22] PCT Filed: Dec. 22, 1993

[86] PCT No.: PCT/EP93/03658

§ 371 Date: Sep. 15, 1995

§ 102(e) Date: Sep. 15, 1995

[87] PCT Pub. No.: WO94/17018

PCT Pub. Date: Aug. 4, 1994

[30] Foreign Application Priority Data

Jan. 20, 1993 [DE] Germany ............... 43 014 58.5

[51] Int. Cl.[6] ............... C07C 5/22
[52] U.S. Cl. ............... 585/471; 546/285; 560/20; 560/255; 564/308; 568/306; 568/632; 505/460; 423/445 B
[58] Field of Search ............... 505/460; 423/445 B; 585/471; 546/285; 560/20, 255; 564/308; 568/306, 632

[56] References Cited

FOREIGN PATENT DOCUMENTS 0 546 718   6/1993   European Pat. Off. .

OTHER PUBLICATIONS

Wudl, F. Acc. Chem. Res. 1992, 25, pp. 157–161.
G. S. Hammond et al., "Fullerenes", ACS Symposium Series 481, Chapter 11: Survey of Chemical Reactivity of C60' Electrophile and Dieno–polar–ophile Par Excellence American Chemical Society, Washington, D.C., 1992, pp. 161–175.
Chemical Reviews, vol. 70, No. 4, published in 1970 I. L. Klundt "Benzocyclobutene and its derivatives" pp. 471–487.

Primary Examiner—C. Warren Ivy
Assistant Examiner—Garth M. Dahlen
Attorney, Agent, or Firm—Frommer Lawrence Haug LLP

[57] ABSTRACT

A fullerene derivative of the formula I

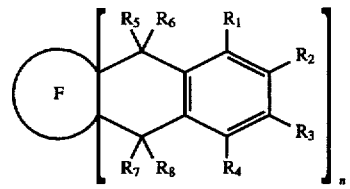

where the symbols and indices have the following meanings:

Ⓕ is a fullerene radical of the formula $(C_{20+2m})$, where m is a number from 1 to 50

$R^1$ to $R^8$ are identical or different and are each H, $CO_2R^9$, CN, $COR^{10}$, Cl, Br, I, F, $OR^{11}$, $C_1$–$C_{20}$-alkyl, phenyl or H, $R^1$–$R^4$ and/or $R^5$, $R^7$ can also be part of a cycloalipathic, cycloaromatic or cycloheteroaromatic system which in turn is substituted by $C_1$–$C_{20}$-alkyl, aryl, carboxyl, carbonyl, alkoxy, aryloxy, halogen, nitro, alcohol or amine, or $R^1$ and $R^2$, $R^2$ and $R^3$, $R^3$ and $R^4$ can together be

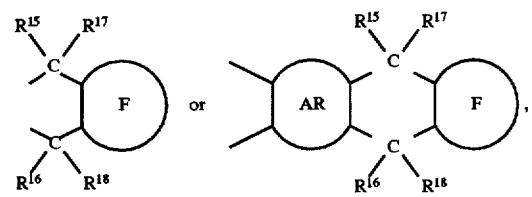

where $R^{15}$–$R^{18}$ are each H, $C_1$–$C_{20}$-alkyl, F, Cl, Br, I or phenyl, and Ⓐ🅡 is the radical of a fused cyclo-aromatic system, and n is from 1 to 20 and a process for its preparation.

4 Claims, No Drawings

THERMALLY STABLE FULLERENE DERIVATIVES AND PROCESS FOR PRODUCING THE SAME

RELATED APPLICATIONS

This application claims priority to German Application No. P 43 01 458.5, filed Jan. 20, 1993, and to International Application No. PCT/EP93/03658, filed Dec. 22, 1993, both incorporated herein by reference.

Several publications are referenced in this application. These references describe the state of the art to which this invention pertains, and are incorporated herein by reference.

BACKGROUND OF THE INVENTION

Fullerenes are cage-like carbon allotropes of the formula ($C_{20+2m}$) (where m=a natural number). They contain twelve five-membered rings and any number, but at least two, six-membered rings of carbon atoms.

Although this class of compounds was not discovered until 1985 by Kroto and Smalley (Nature, 1985, 318, 162) and Krätschmer and Huffmann did not report the preparation of macroscopic amounts of $C_{60}$ until 1990 (Nature, 1990, 347, 354), such compounds have very quickly attracted wide interest and within a very short time have become the subject of numerous research studies (see, for example, G. S. Hammond, V. J. Kuck (Editors), "Fullerenes", ACS Symposium Series 481, American Chemical Society, Washington DC 1992 and Accounts of Chemical Research 1992, 25, 98–175).

The use of fullerenes as synthetic building blocks in organic chemistry is beset by great difficulties since, for example, the degree of substitution of fullerenes can be controlled only with difficulty during the formation of derivatives. $C_{60}$ contains 30 double bonds which are in principle available as reaction centers. In addition, a very large number of positional isomers is possible as soon as even only two substituents are present on the fullerene base structure.

Further problems are provided by the low solubility of the fullerenes in all conventional solvents.

However, since there is the expectation of a high potential of this class of substances, for example in the fields of optoelectronics and research on active compounds, efforts have already been made to form derivatives, in particular of $C_{60}$ (see, for example, H. Schwarz, Angew. Chemie, 1992, 104, 301 and F. Wudl et al. in "Fullerenes" G. S. Hammond, V. S. Kuck, eds. ACS Symp. Ser. 481, p. 161, Washington DC 1992 and Accounts of Chemical Research, 1992, 25, 157).

It is already known that fullerenes can be reacted with dienes to give Diels-Alder adducts ("Fullerenes ACS-Symposium Series No. 481, p. 164). The dienophilic reactivity of $C_{60}$ has hitherto been observed only in the reaction with anthracene and furan and also cyclopentadiene. However, all these reactions have a broad product distribution. Furthermore, these products decompose again on heating into their starting compounds.

It is also known that fullerenes can be reacted with diazo compounds in a 1,3 dipolar cycloaddition (e.g. F. Wudl, Acc. Chem. Res., 1992, 25, 157).

It was desirable to synthesize derivatives of fullerenes which are thermally stable, contain the basic fullerene framework, and make possible further reactions at the derivatized position.

DESCRIPTION OF THE INVENTION

It has now been found that well-defined fullerene derivatives can be obtained by reacting fullerene with a compound of the formula

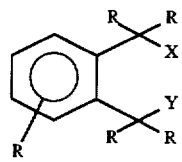

or the formula

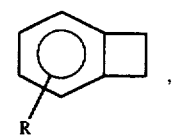

with the aromatic ring system being bonded to the fullerene via a cycloaliphatic 6-membered ring.

The invention accordingly provides a fullerene derivative of the formula I,

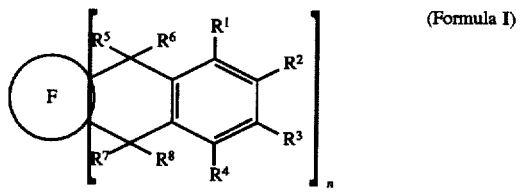

(Formula I)

where the symbols and indices have the following meanings:

(F) is a fullerene radical of the formula ($C_{20+2m}$), where m is a number from 1 to 50

$R^1$ to $R^8$ are identical or different and are each H, $NH_2$, $NR^9R^{10}$, $NR^9H$, $CO_2R^9$, $OCOR^{10}$, CN, $COR^{10}$, Cl, Br, I, F, $OR^{11}$, $CONH_2$, $C_1$–$C_{20}$alkyl which can be substituted by Cl, I, Br and F, $C_3$–$C_8$-cycloalkyl, aryl, heteroaryl, where $R^9$ to $R^{11}$ are each H, $C_1$–$C_{20}$-alkyl which can be substituted by F, Cl, Br or I, pyridinyl or phenyl which in turn can be substituted by F, Cl, Br, I, nitro, amino, $C_1$–$C_{20}$-alkylamino, $C_6$–$C_{14}$-arylamino, $C_1$–$C_{20}$-alkoxy or $C_6$–$C_{14}$-aryloxy, or —$(CH_2)_j$—$CO_2H$ having j=1 to 10, $R^1$–$R^4$ and/or $R^5$, $R^7$ can also be part of a cycloaliphatic, aromatic or heteroaromatic system which is in turn substituted by $C_1$–$C_{20}$-alkyl, aryl, carboxyl, carbonyl, alkoxy, aryloxy, F, Cl, Br, I, nitro, alcohol or amine, or $R^1$ and $R^2$, $R^2$ and $R^3$, $R^3$ and $R^4$ can in each case together be

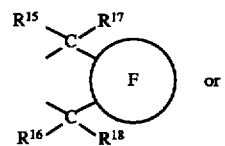

or

-continued

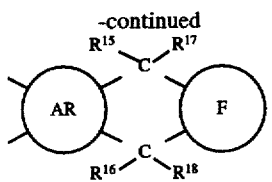

where $R^{15}$–$R^{18}$ are each H, $C_1$–$C_{20}$-alkyl, F, Cl, Br, I or phenyl, and (AR) is the radical of a fused aromatic system, $R^5$ to $R^8$ can also be the structural element of the formula V

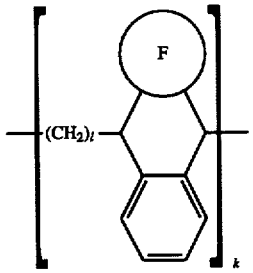

where i is a number from 2 to 20 and k is a number greater than 1, and $R^5$ and $R^7$ can together also be an —O— bridge, n is from 1 to 20.

Preference is given to compounds of the formula I in which the symbols and indices have the following meanings:

(F) is a fullerene radical of the formula $(C_{20+2m})$, where m is 20, 25, 28, 29, 31 or 32, $R^1$ to $R^8$ are as defined above, n is 1 or 2.

Particular preference is given to compounds of the formula I in which the symbols and indices have the following meanings:

(F) is $C_{60}$ or $C_{70}$ $R^1$ to $R^4$ are identical or different and are each H, $NH_2$, $COR^9$, $CO_2R^{10}$, —O—$R^{11}$, $OCOR^{10}$ or $C_1$–$C_{10}$-alkyl which can be substituted by F, Cl, Br or I, where $R^9$ to $R^{11}$ are each H, $(C_1$–$C_{10})$-alkyl which can be substituted by F, Cl or Br, pyridinyl, phenyl which can be substituted by F, Cl, Br, nitro, amino, $C_1$–$C_{10}$-alkylamino, $C_6$–$C_{14}$-arylamino, $C_1$–$C_{10}$-alkoxy or $C_6$–$C_{14}$-aryloxy, or —$(CH_2)_j$—$CO_2H$ having j=1 to 10, or $R^2$ and $R^3$ together are

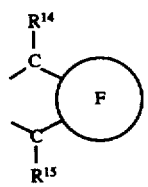

or

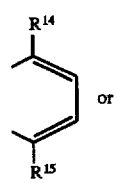

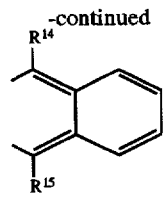

where $R^{14}$ and/or $R^{15}$ are each H, phenyl or $(C_1$–$C_{10})$ alkyl, and $R^5$ to $R^8$ are identical or different and are each H, F, Cl, Br, $(C_1$–$C_{12})$-alkyl or a structural element of the formula V having i=4 to 12 and k being a number greater than 1 and n is 1 or 2.

Very particular preference is given to compounds of the formula I in which the symbols and indices have the following meanings:

(F) is $C_{60}$ and $R^1$ to $R^4$ and also $R^5$ to $R^8$ have the last-named meanings.

The bonding of the structural element

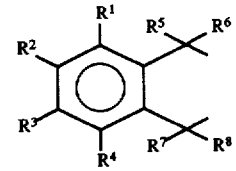

from formula I to the fullerene occurs via two adjacent carbon atoms in the fullerene molecule which in turn can be represented as structural element by the formula II a or II b

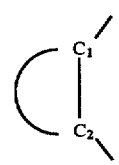

IIa

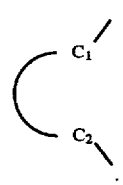

IIb

The compounds of the invention having the formula I are prepared, for example, by cycloaddition of the compounds III or IV to a fullerene molecule.

This can be carried out in principle by methods known in the literature for the addition of a diene to olefins, as described, for example, in I. L. Klundt, Chemical Reviews, 1970, Vol. 70, No. 4, 471–487 and R. P. Thummel, Acc. Chem. Res. 1980, 13, 70–76. Bis(bromomethyl)benzene derivatives (III) can be prepared as described, for example, in I. L. Klundt, Chemical Reviews, 1970, Vol. 70, No. 4, 471–487 and R. P. Thummel, Acc. Chem. Res. 1980, 13, 70–76. 1,3-dihydroisothianaphthene-2,2-dioxide derivatives (III, Y=$SO_2$), benzocyclobutene derivatives IV are prepared as described in A. P. Cove, J. Org. Chem. 1969, 34, 538 or J. A. Chem. Soc. 1959, 81, 4266.

Preference is given to a process for preparing compounds of the formula I, in which a fullerene of the formula $C_{(20+2m)}$ (m=0, 1, 2, ...) is reacted in an aprotic organic solvent such as toluene, CCl₄, CH₂Cl₂, benzene, chlorobenzene with substituted ortho-alkylbenzenes of the formula III,

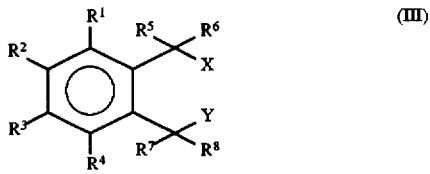

where $R^1$ to $R^8$ are as defined above and X and Y are each halogen or together are $SO_2$, $CO_2$ or $N_2$, or else compounds of the formula IV

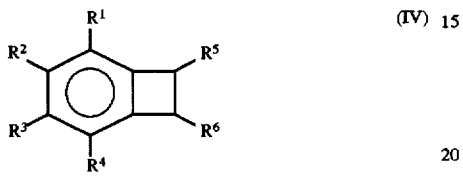

where $R^1$ to $R^6$ are as defined above.

The reaction can be carried out in a temperature range from 100° to 300° C., preferably from 100° to 210° C. To prepare compounds of the formula I having n=1, the starting compounds are preferably used in stoichiometric amounts.

The fullerene used is very particularly preferably pure $C_{60}$ and/or $C_{70}$, but also crude fullerenes which contain a mixture of $C_{60}$ and $C_{70}$ as main components. However, it is also possible to use all other conceivable fullerenes or fullerene derivatives.

The fullerenes are, in part, commercially available or can be obtained by production of fullerene black in an electric arc process using subsequent extraction with a nonpolar organic solvent (crude fullerenes), as described in, for example, WO 92/09279. The further fine separation can be carried out by column chromatography.

EXAMPLES

The compounds of the invention having the formula I can be used in optoelectronic components.

The invention is illustrated by the following examples. The following examples are intended neither to define nor limit the invention in any manner.

Reaction of Fullerenes with ortho-guinodimethane derivatives

A. Reaction of $C_{60}$ via base-induced 1,4-elimination of 1,2-bis(bromomethyl)aromatics General procedure:

$C_{60}$ (100 mg=0.139 mmol), 1,2-bis(bromomethyl) aromatic (0.139 mmol), KI (50 mg=0.3 mmol) and [18]crown-6 (300 mg=1.13 mmol) in 50 ml of toluene are heated for a number of hours, with the solution changing color. The crude product obtained after the usual workup can be purified, for example, by chromatography.

Example A.1: m=10; n=1, $R^1$–$R^8$=H.

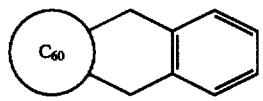

Reaction time: 6 hours
Yield: 88% (based on $C_{60}$ reacted)
Characterization:
¹H-NMR (500 MHz, $C_2Cl_4D_2$, 28° C.): δ=4.46 (d broadened, 2 H; CH₂); 4.82 (d broadened, 2 H; CH₂); 7.57–7.59 and 7.69–7.71 (m, AA'BB' system of the arene); measurement at 125° C.: δ=4.70 (s, 4H; CH₂);
¹³C-NMR (125 MHz, $C_2Cl_4D_2$, 80° C., J-modulated spin echo for ¹³C): δ=45.28 (benzyl C); 66.09 (aliphatic quaternary $C_{60}$ carbon atoms); 128.02 and 128.09 (H-substituted aromatic carbon atoms), 135.76, 138.21, 140.20, 141.66, 142.13, 142.30, 142.62, 143.17, 144.78, 145.42, 145.49, 145.51, 145.85, 146.30, 146.52, 147.76 and 156.93 (17 arene signals). MS(FD): m/e 824 UV/VIS (CHCl₃): Similar to $C_{60}$, but less structured; weak maximum at 435 nm.

Example A.2: m=20; n=1; $R^1$ and $R^4$=CH3; $R^2$, $R^3$ and $R^5$–$R^8$=H.

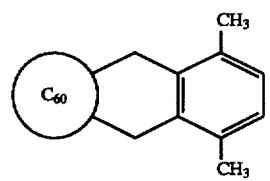

Reaction time: 8 hours
Yield: 86% (based on $C_{60}$ reacted)
Characterization:
¹H-NMR (500 MHz, $C_2Cl_4D_2$, 28° C.), δ=2.58 (s, 6H, CH₃); 4.09 (broadened, 4H; CH₂); 7.32 (s, 2H of the arene);
¹³C-NMR (125 MHz, $C_2D_2Cl_4$, 28° C.), δ=29.8 (methyl), 41.2 (CH₂), 66 (aliphatic quaternary $C_{60}$ carbon atoms), 128.9 (H-substituted aromatic carbon atoms); 133.2; 136.7; 140.2; 141.6; 142.1; 142.3; 142.6; 143.1; 144.8; 145.5; 146.3; 146.5; 147.7; 156.8

MS (FD): m/e 852 UV/VIS (CHCl₃): Similar to $C_{60}$, but less structured; weak maximum at 435 nm.

Example A.3: m=20, n=1, $R^1$ and $R^3$–$R^8$=H; $R^2$=OCH3.

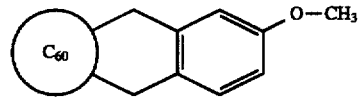

Reaction time: 12 hours
Yield: 82% (based on $C_{60}$ reacted)
Characterization:
¹H-NMR (500 MHz, $C_2Cl_4D_2$, 28° C.), δ=3.97 (s; OCH₃) 4.41–4.55 (m; broadened; CH₂) 4.76–4.80 (m; broadened; CH₂); 7.08–7.10 (dd; arene H); 7.26 (d; arene H); 7.60–7.62 (d, arene H).

MS (FD): m/e 854 UV/VIS (CHCl₃): Similar to $C_{60}$, but less structured; weak maximum at 435 nm.

B. Reaction of $C_{60}$ via thermal $SO_2$ extrusion from compounds of the formula III Example B.1: m=20; n=1; $R^1$–$R^8$=H:

Experimental procedure:

$C_{60}$ (75 mg=0.104 mmol) and 1,3-dihydroisothianaphthene-2,2-dioxide (25 mg=0.149 mmol) in 20 ml of 1,2,4-trichlorobenzene are heated under reflux for 2 days, with the reaction solution becoming brown. The solution is admixed with 40 ml of ethanol and the brown precipitated reaction product is filtered off. The reaction product can be separated, for example by means of chromatography over polystyrene gel crosslinked with divinylbenzene (100 Å, 5 μm) using CHCl₃ or toluene as eluants, into unreacted $C_{60}$, monoaddition product (n=1) and very small amounts of diaddition product (n=2). The yield of monoaddition product (n=1) is 81% (based on $C_{60}$ reacted). For the characterization see Example A.1.

Example B.2: m=20; n=1; $R^1$ and $R^4$=phenyl; $R^5$–$R^8$=H; $R^2$ and $R^3$=part of a fused-on benzene ring.

Experimental procedure:

C$_{60}$ (80 mg=0.111 mmol) and 4,9-diphenyl-1,3-dihydronaphtho[2,3-c]thiophene-2,2-dioxide (62 mg=0.167 mmol) in 20 ml of 1,2,4-trichlorobenzene are heated under reflux for 3 days, with the reaction solution becoming brown. The reaction mixture is worked up in a similar manner to Example B.1.

The yield of monoaddition product (n=1) is 75% (based on C$_{60}$ reacted)

Characterization of the monoaddition product (n=1):

FD mass spectroscopy: 1025.98 (100%, M$^+$)

$^1$H-NMR (500 MHz, CDCl$_3$), 4.47 ppm (d, 2H); 4.75 ppm (d, 2H); 7.22–7.7 ppm (14H) $^{13}$C-NMR (125 MHz, CDCl$_3$): 42.4 ppm (CH$_2$); 65.72 ppm (quaternary aliphatic carbon atom of C$_{60}$) UV (CHCl$_3$): weak absorption maximum at 432.5 nm (characteristic of C$_{60}$ monoaddition products)

C. Reaction of C$_{60}$ via thermal ring opening of benzocyclobutene derivatives of the formula IV Example C.1: m=20; n=1; R$^1$–R$^8$=H:

Experimental procedure:

C$_{60}$ (100 mg=0.139 mmol) and benzocyclobutane (preparation according to P. Schiess et al. Tetrahedron Letters 1982, 23, 3665) (16 mg=0.154 mmol) in 20 ml of 1,2-dichlorobenzene are heated under reflux for 3 hours, with the reaction solution becoming brown. The reaction mixture is worked up in a similar manner to Example B.1. The yield of monoaddition product (n=1) is 90% (based on C$_{60}$ reacted). For the characterization see Example A.1.

Example C.2: m=20; n=1; R$^5$ and R$^7$=Br; R$^1$–R$^4$, R$^6$ and R$^8$=H.

Experimental procedure:

C$_{60}$ (100 mg=0.139 mmol) and 1,2-dibromobenzocyclobutane (preparation according to M. P. Cava et al. J. Am. Chem. Soc. 1959, 81, 6458) (40.5 mg=0.155 mmol) in 20 ml of 1,2-dichlorobenzene are heated at 130° C. for 2 hours, with the reaction solution becoming brown. The reaction mixture is worked up in a similar manner to Example B.1.

The yield of monoaddition product (n=1) is 72% (based on C$_{60}$ reacted).

Characterization of the monoaddition product (n=1):

FD mass spectroscopy: 981.7 (100%, M$^+$); 901.8 (45%, M$^+$, Br); 821.9 (87%, M$^+$, Br$_2$)

$^1$H-NMR (500 MHz, CDCl$_3$), 6.96 ppm (s, 1H, CHBr); 7.66 ppm (t, 1H, CH); 7.76 ppm (s+t, 2H, CH); 8.04 ppm (s, 1H, CHBr); 8.24 ppm (d, 1H, CH)

$^{13}$C-NMR (125 MHz, CDCl$_3$): 56.26 ppm (CHBr); 57.07 ppm (CHBr); 127.13 ppm (aromatic CH); 129.22 ppm (aromatic CH); 130.45 ppm (aromatic CH); 131.01 ppm (aromatic CH); 155.14, 152.61, 152.53, 151.74, 147.87, 147.77, 147.75, 147.54, 146.75, 146.60, 146.57, 146.56, 146.36, 146.26, 146.15, 146.08, 145.84, 145.83, 145.59, 145.54, 145.50, 145.43, 145.35, 145.30, 144.78, 144.63, 144.37, 144.02, 144.00, 143.97, 143.12, 142.84, 142.78, 142.70, 142.68, 142.59, 142.52, 142.37, 142.31, 142.12, 141.69, 141.51, 141.50, 141.42, 141.41, 141.38, 141.32, 139.97, 138.53, 138.12, 136.64, 136.17, 136.16, 136.02, 135.37 ppm (55 quaternary non-aliphatic carbon atoms). UV (CHCl$_3$): weak absorption maximum at 432.5 nm Example C.3: m=20; n=1; R$^1$, R$^3$, R$^4$, R$^5$ and R$^6$=H; R$^2$=4-fluoro-3-nitrobenzoyl.

Experimental procedure:

1055 mg of C$_{60}$ (1.465 mmol) and 336 mg of 4-(4-fluoro-3-nitrobenzoyl)benzocyclobutene (1.2398 mmol) in 200 ml of 1,2,4-trichlorobenzene were heated under reflux for 7 hours. The solvent was distilled off in vacuo (20 mbar, 130° C.), the distillation residue was suspended in 200 ml of CHCl$_3$, filtered from undissolved C$_{60}$ and worked up by chromatography. This gave 72% of the monoadduct, 19% of the diadduct and 9% of unreacted C$_{60}$.

Characterization of the monoaddition product (n=1).

MS (FD: m/e 991.1 ([M]+, 100%) $^1$H-NMR (500 MHz, C$_2$D$_2$Cl$_4$, 28° C.): d=4.48 (d (b), 2H, CH$_2$), 4.81 (d (b), 2H, CH$_2$), 7.45 (t, 1H, 9 and 10 Hz, i), 7.8 (d, 1H, 8 Hz, f), 7.89 (d, 1H, 8 Hz, g), 8.04 (s (b), 1H, e), 8.18 (m, 1H, h), 8.53 ppm (dd, 1H, 2 and 7 Hz, k) $^{13}$C-NMR (125 MHz, C$_2$D$_2$Cl$_4$, 28° C.; J-modulated spin echo for $^{13}$C): d=47.97, 48.19 (CH$_2$), 68.51, 68.56 (sp$^3$ C$_{60}$ carbon atoms), 122.08, 122.25, 128.49, 131.23, 131.40, 131.66, 132.23, 132.29, 132.83 (b), 133.06, 140.10, 140.18 (all CH), 119.4, 119.65, 126.65, 136.75, 137.5, 137.52, 138.69, 141.06, 142.20, 143.20 (b, plurality of superimposed signals), 144.69 (b, plurality of superimposed signals), 145.11 (b, plurality of superimposed signals), 145.17, 145.19, 145.64, 146.16 (b, plurality of superimposed signals), 147.42, 147.72, 147.75, 148.52 (b, plurality of superimposed signals), 149.32, 149.53, 149.55, 150.75, 150.77 (all quaternary non-aliphatic carbon atoms), 195.90 ppm (CO) UV/VIS (CHCl$_3$): weak absorption maximum at about 435 nm.

Example C.4: m=20; n=1, R$^5$=OCOCH$_3$, R$^1$–R$^4$=H, R$^6$–R$^8$=H.

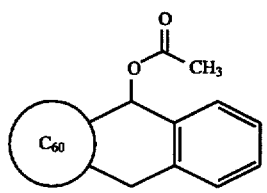

Experimental procedure:

400 mg (2.37●10⁻³ mol) ±-benzocyclobuten-7-yl acetate were heated under reflux with 813 mg (1.13●10⁻³ mol) of $C_{60}$ fullerene in 75 ml of 1,2,4-trichlorobenzene for 5 hours. The solvent was subsequently distilled off and the solid obtained was dissolved in chloroform. The solution was filtered through a 0.25 μm teflon membrane filter and purified by chromatography over polystyrene gel. Yield: 170 mg of monoadduct, 648 mg of diadduct and 374 mg of triadduct.

Characterization of the monoaddition product (n=1):

UV/VIS: (n=1) shows an absorption band at 430 nm. FD mass spectroscopy: m/e=882.2 (M⁺ of (n=1), 66%), 1044.3 (M⁺ of (n=2), 100%), 1206.3 (M⁺ of (n=3), 68%), 1369.5 (M⁺ of (n=4), 4%) (n=1) (mixture of two diastereomers (a) and (b)):

¹H-NMR (500 MHz, $C_2D_2Cl_4$, 28° C.): δ=2.283 (s, 3H, $CH_3$, a), 2.288 (s, 3H, $CH_3$, a'), 4.33 (d, 1H, $CH_2$, 14 Hz, b), 4.45 (d, 1H, $CH_2$, 14 Hz, b'), 4.83 (d, 1H, $CH_2$, 14 Hz, c), 5.31 (d, 1H, $CH_2$, 14 Hz, c'), 7.21 (s, 1H, CHOR, d), 7.36 (s, 1H, CHOR, d'), 7.49–7.64 (m, 2×4H), CH, e) ¹³C-NMR (500 MHz, $C_2D_2Cl_4$, 28° C.; J-modulated spin echo for ¹³C): δ=44.20, 44.56 (aliphatic, secondary carbon atoms), 64.31, 66.37, 69.51, 69.79 (aliphatic, quaternary $C_{60}$ atoms, diastereomers), 120.59, 121.58 (quaternary aromatic carbon atoms), 128.09, 128.53, 130.00, 131.22, 131.27, 132.37 (ternary aromatic carbon atoms), 134.22, 137.59, 137.65 (quaternary aromatic carbon atoms), 141.78, 141.87, 142.10, 142.27, 142.72, 142.78, 145.53, 145.59, 145.62, 145.77, 145.84, 146.38, 146.57, 146.64, 146.71, 152.55, 155.75, 156.97, 161.64 (quaternary $C_{60}$ atoms, in each case a plurality of superimposed signals), 170.57, 170.75 (C=O)

Example C.5: m=20; n=1;

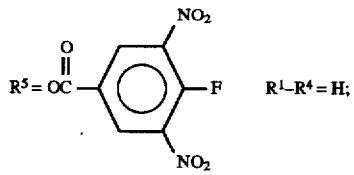

R¹–R⁴ = H;

R⁶–R⁸ = H.

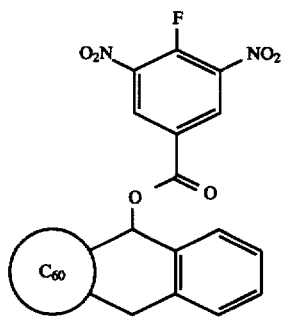

Experimental procedure:

400 mg (1.2●10⁻³ mol) of ±-benzocyclobuten-7-ol 4-fluoro-3,5-dinitrobenzoate were heated under reflux together with 596 mg (8.28●10⁻⁴ mol) of $C_{60}$ fullerene in 75 ml of 1,2,4-trichlorobenzene for 5 hours. The solvent was subsequently distilled off and the solid obtained was dissolved in chloroform. The solution was filtered through a 0.25 μm teflon membrane filter. The adducts were separated by chromatography over polystyrene gel. In this way, 270 mg of monoadduct, 184 mg of diadduct and 95 mg of triadduct were able to be isolated.

Characterization of the monoaddition product (n=1):

UV/VIS: (n=1) shows an absorption band at 430 nm.

FD mass spectroscopy: m/e=1052 (M⁺ of (n=1), 78%), 1384 (M⁺ of (n=2), 100%), 1716 (M⁺ of (n=3), 16%)

(n=1) (mixture of two diastereomers (a) and (b)): ¹³C-NMR (500 MHz, $CDCl_3$, J-modulated spin echo): δ=44.02, 44.82 (aliphatic, secondary carbon atoms), 63.84, 66.14, 68.17, 69.22 (aliphatic, quaternary $C_{60}$ atoms, diasteromers), 120.59, 121.58 (quaternary aromatic carbon atoms), 128.09, 128.53, 130.00, 131.22, 131.27, 132.37 (ternary aromatic carbon atoms), 134.22, 137.59, 137.65 (quaternary aromatic carbon atoms), 141.78, 141.87, 142.10, 142.27, 142.72, 142.78, 145.53, 145.59, 145.62, 145.77, 145.84, 146.38, 146.57, 146.64, 146.71, 152.55, 155.75, 156.97 (quaternary $C_{60}$ atoms, in each case a plurality of superimposed signals), 161.64 (C=O)

(n=1): ¹H-NMR (500 MHz, $CDCl_3$, 28° C.): δ=4.58 (d, 1H, $CH_2$, 14 Hz, a), 4.64 (d, 1H, $CH_2$, 16 Hz, a'), 4.99 (d, 1H, $CH_2$, 14 Hz, b'), 5.4 (d, 1H, $CH_2$, 14 Hz, b), 7.55–7.85 (m, 4H, CH, c), 8.01 (s, 1H, CHOR, d), 8.03 (s, 1H, CHOR, d'), 9.12 (s, 2H, CH, e), 9.25 (s, 2H, CH, e')

Example C.6: m=20; n=1;

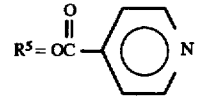

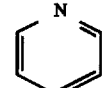

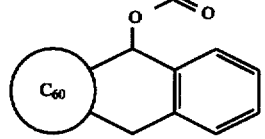

Experimental procedure:

80 mg (3.55●10⁻⁴ mol) of ±-benzocyclobuten-7-yl isonicotinate were heated under reflux together with 500 mg (6.94●10⁻⁴ mol) of $C_{60}$ fullerene in 75 ml of 1,2,4-trichlorobenzene for 5 hours. The solvent was subsequently distilled off and the solid obtained was dissolved in chloroform. The solution was filtered through a 0.25 μm teflon membrane filter. The adducts were subsequently separated over polystyrene gel. Yield: 288 mg of monoadduct and 648 mg of diadduct.

Characterization of the monoaddition product (n=1):

UV/VIS: (n=1) shows an absorption band at 430 nm. FD mass spectroscopy: m/e=945.1 (M⁺ of (n=1), 100%), 1170.2 (M⁺ of (n=2), 20%), 1395.3 (M⁺ of (n=3), 2%) (n=1): ¹³C-NMR (500 MHz, $C_2D_2Cl_4$, 28° C., J-modulated spin echo): δ=44.5 (aliphatic, secondary carbon atoms), 64.23 (aliphatic, quaternary $C_{60}$ atoms), 123.43, 129.35, 128.34, 130.40, 131.12 (CH, aromatic carbon atoms), 134.78, 137.98, 140.23, 140.40, 140.61, 140.65, 141.76, 141.82, 141.92, 142.08, 142.28 (a plurality of superimposed signals), 142.82 (a plurality of superimposed signals), 142.88, 142.93 (a plurality of superimposed signals), 143.34, 143.38, 144.96 (a plurality of superimposed signals), 145.01 (a plurality of superimposed signals), 145.40 (a plurality of superimposed signals), 145.64, 145.72, 145.76, 145.82, 145.89, 145.91, 145.96, 146.81 (a plurality of superimposed signals), 148.05 (a plurality of superimposed signals), 151.25, 153.18, 153.76, 157.19, 157.27 (all quaternary $C_{60}$ atoms), 151.10 (aromatic carbon atoms adjacent to the nitrogen in the pyridine radical), 163.5 (C=O) (n=1): $^1$H-NMR (500 MHz, $C_2D_2Cl_4$, 28° C., mixture of two diastereomers (a) and (b)): δ=4.52 (d, 1H, $CH_2$, 14 Hz, a), 4.58 (d, 1H, $CH_2$, 14 Hz, a'), 4.97 (d, 1H, $CH_2$, 14 Hz, b'), 5.44 (d, 1H, $CH_2$, 14 Hz, b), 7.60–7.67 (m, 4H, CH, c), 7.72 (s, 1H, CHOR, d), 7.74 (s, 1H, CHOR, d'), 8.00 (d, 2H, CH, 6 Hz, e'), 8.12 (d, 2H, CH, 6 Hz, e), 8.81 (d, 2H, CH, 5 Hz, f), 8.89 (d, 2H, CH, 6 Hz, f)

D. Reaction of $C_{60}$ via thermal $CO_2$ extrusion from compounds of the formula III Example D.1: m=20; n=1; $R^1$, $R^4$–$R^8$=H; $R^2$, $R^3$=OCH$_3$; X=O; Y=C=O

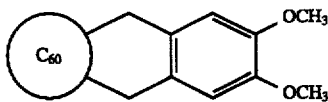

127 mg of 6,7-dimethoxy-3-isochromanone (0.65 mmol) and 360 mg of $C_{60}$ fullerene (0.5 mmol) were heated for 24 hours under reflux in 80 ml of 1,2,4-trichlorobenzene.

The solvent was distilled off and the mixture was worked up by chromatography. This gave 47% of the monoadduct, 22% of the diadduct and 30% of unreacted $C_{60}$.

Characterization of the monoaddition product (n=1)

MS (FD): m/e 887.4 ([M]$^+$ of (n=1), 100), 903 ([M+16]$^+$, 5)

$^1$H-NMR (500 MHz, $C_2D_2Cl_4$, 28° C.): d=4.01 (s, 6H, —OCH$_3$), 4.37 (d(b), 2H, $CH_2$, 4.74 (d(b), 2H, $CH_2$), 7.20 (s, 2H) $^{13}$C-NMR (125 MHz, $C_2D_2Cl_4$, 28° C.; J-modulated spin echo for $^{13}$C): d=58.2 (CH$_3$), 46.62 (CH$_2$), 67.94 (sp$^3$ $C_{60}$ carbon atoms), 113.57 (CH, aromatic), 132.06, 141.83 (b), 143.33, 143.80, 144.02, 144.29, 144.84, 146.45 (b), 147.18, 147.29, 147.57, 147.96, 148.20, 149.40, 150.34, 158.36 (b) ppm (all quaternary nonaliphatic carbon atoms) UV/VIS (CHCl$_3$): weak absorption maximum at 435 nm Example E: m=20; n=1; $R^1$, $R^3$–$R^8$=H, $R^2$=

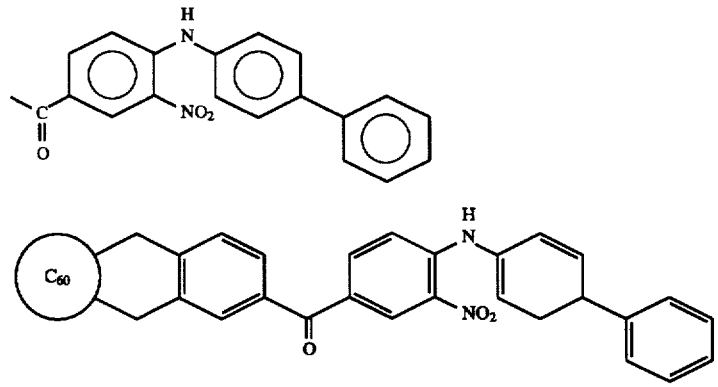

11 mg (1.1●10$^{-2}$ mmol) of the fluoro-nitro derivative from Example C.3 were dissolved in 7 ml of dry dimethylacetamide and admixed with 59.1 mg (0.35 mmol) of 4-aminobiphenyl. The reaction mixture was heated at 65° C. for one week and subsequently admixed with 30 ml of water. After some time, a floccular, brown solid precipitated from the mixture, and this was filtered off through a 0.25 μm teflon membrane filter. The filter residue was eluted from the filter using chloroform and was worked up by chromatography. The yield was almost quantitative.

$^1$H-NMR (500 MHz, $C_2D_2Cl_4$, 28° C.): δ=4.48 (b, 2H, $CH_2$, a), 4.82 (b, 2H, $CH_2$, a), 7.3–7.43 (m, 6H, CH, b, c, d, e), 7.57 (d, 2H, CH, 7.3 Hz, f), 7.65 (d, 2H, CH, 8.4 Hz, g), 7.78 Hz, h), 7.89 (dd, 1H, CH, 1.5 Hz and 8.0 Hz, i), 7.98 (dd, 1H, CH, 2 Hz and 8.0 Hz, j), 8.02 (s, 1H, CH, k), 9.85 (d, 1H, CH, 2 Hz, l)

$^{13}$C-NMR (J-modulated spin echo for $^{13}$C; 500 MHz, $C_2D_2Cl_4$, 28° C.): δ=48.04, 48.18 (CH$_2$), 68.63, 68.68 (quaternary aliphatic $C_{60}$ atoms), 119.3, 128.42, 128.49, 130.11, 131.4, 131.7, 132.12, 132.23, 132.65, 133.62, 139.87 (all CH), 129.75, 134.96, 139.61, 139.99, 141.06, 141.8, 142.77, 142.86, 143.24 (b, a plurality of superimposed signals), 144.66 (b, a plurality of superimposed signals), 145.11, 145.21, 145.25, 145.61, 146.16 (b, a plurality of superimposed signals), 146.27, 147.72, 147.77, 148.51, 149.01, 149.29 (b, a plurality of superimposed signals), 149.54 (b, a plurality of superimposed signals), 150.73, 150.76 (all quaternary carbon atoms), 196.37 (C=O)

UV/VIS: weak absorption maximum at 430 nm FD mass spectrum: m/e=1139.6 (M$^+$, 100%), 720 (M$^+$ of $C_{60}$, 5%), 570.2 (M$^{2+}$, 15%)

We claim:

1. A fullerene derivative of the formula I (Formula I)

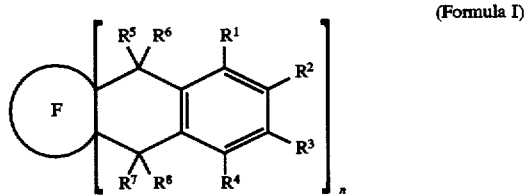

where the symbols and indices have the following meanings:

Ⓕ is a fullerene radical of the formula ($C_{20+2m}$), where m is a number from 1 to 50

$R^1$ to $R^8$ are identical or different and are each H, NH$_2$, CO$_2R^9$, CN, OCOR$^{10}$, COR$^{10}$, Cl, BR, I, F, OR$^{11}$, $CONH_2$, $C_1$–$C_{20}$-alkyl which can be substituted by Cl, I, Br and F, $C^3$–$C_8$-cycloalkyl, aryl, heteroaryl, where $R^9$ to $R^{11}$ are each H, $C_1$–$C_{20}$-alkyl which can be substituted by F, Cl, Br or I, pyridinyl or phenyl which in turn can be substituted by F, Cl, Br, I, nitro, amino, $C_1$–$C_{20}$-alkylamino, $C_6$–$C_{14}$-arylamino, $C_1$–$C_{20}$-alkylamino, $C_6$–$C_{14}$-arylamino, $C_1$–$C_{20}$-alkoxy or $C_6$–$C_{14}$-aryloxy, or —$(CH_2)_J$—$CO_2H$ having J=1 to 10, $R^1$–$R^4$ and/or $R^5$, $R^7$ can also be part of a cycloaliphatic, aromatic or heteroaromatic system which is in turn substituted by $C_1$–$C_{20}$-alkyl, aryl, carboxyl, carbonyl, alkoxy, aryloxy, F, Cl, Br, I, nitro, alcohol or amine, or $R^1$ and $R^2$, $R^2$ and $R^3$, $R^3$ and $R^4$ can in each case together be

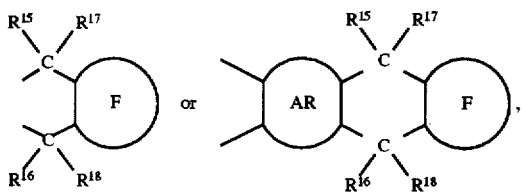

where $R^{15}$–$R^{18}$ are each H, $C_1$–$C_{20}$-alkyl, F, Cl, Br, I or phenyl, and AR is the radical of a fused aromatic system, and $R^5$ and $R^7$ can together also be an —O— bridge, n is from 1 to 20.

2. A fullerene derivative as claimed in claim 1, wherein the symbols and indices have the following meanings:

Ⓕ is a fullerene derivative of the formula ($C_{20+2m}$) in which m is 20, 25, 28, 29, 31 or 32,
n is 1 or 2.

3. A fullerene derivative as claimed in claim 1, wherein the symbols and indices have the following meanings:

F is $C_{60}$ or $C_{70}$ $R^1$ to $R^4$ are identical or different and are each H, $NH_2$, $COR^9$, $CO_2R^{10}$, —O—$R^{11}$, $OCOR^{10}$ or $C_1$–$C_{10}$-alkyl which can be substituted by F, Cl, Br or I, where $R^9$ to $R^{11}$ are each H, $(C_1$–$C_{10})$-alkyl which can be substituted by F, Cl or Br, pyridinyl, phenyl which can be substituted by F, Cl, BR, nitro, amino, $C_1$–$C_{10}$-alkylamino, $C_6$–$C_{14}$-arylamino, $C_1$–$C_{10}$-alkoxy or $C_6$–$C_{14}$-aryloxy, or —$(CH_2)_j$—$CO_2H$ having j=1 to 10, or $R^2$ and $R^3$ together are

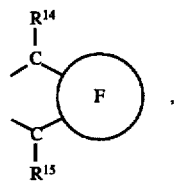

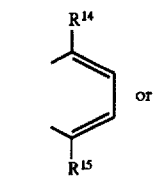

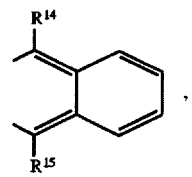

where $R^{14}$ and/or $R^{15}$ are each H, phenyl or $(C_1$–$C_{10})$-alkyl, and $R^5$ to $R^8$ are identical or different and are each H, F, Cl, Br, or $(C_1$–$C_{12})$-alkyl and n is 1 or 2.

4. A fullerene derivative as claimed in claim 3, wherein Ⓕ is $C_{60}$.

* * * * *